United States Patent [19]

Bortinger

[11] Patent Number: 6,107,234

[45] Date of Patent: Aug. 22, 2000

[54] PHOSPHORUS/VANADIUM MALEIC ANHYDRIDE CATALYST PREPARATION

[75] Inventor: Arie Bortinger, Ridgewood, N.J.

[73] Assignee: Scientific Design Company, Inc., Little Ferry, N.J.

[21] Appl. No.: 09/239,651

[22] Filed: Jan. 29, 1999

[51] Int. Cl.[7] .......................... B01J 27/198; B01J 27/188; B01J 27/19; B01J 27/192

[52] U.S. Cl. .......................... 502/209; 502/210; 502/211; 502/212

[58] Field of Search ..................................... 502/209–212

[56] References Cited

U.S. PATENT DOCUMENTS

| | | | |
|---|---|---|---|
| 3,980,585 | 9/1976 | Kerr et al. | 252/437 |
| 4,043,943 | 8/1977 | Schneider | 252/437 |
| 4,056,487 | 11/1977 | Kerr | 252/435 |
| 4,147,661 | 4/1979 | Higgins et al. | 252/435 |
| 4,283,307 | 8/1981 | Barone et al. | 252/432 |
| 4,418,003 | 11/1983 | Udovich et al. | 502/209 |
| 4,515,904 | 5/1985 | Edwards | 502/209 |
| 4,569,925 | 2/1986 | Yang et al. | 502/209 |
| 5,137,860 | 8/1992 | Ebner et al. | 502/209 |
| 5,280,003 | 1/1994 | Bortinger | 502/209 |
| 5,288,880 | 2/1994 | Matsuura | 549/260 |
| 5,296,436 | 3/1994 | Bortinger | 502/209 |
| 5,480,853 | 1/1996 | Bortinger | 502/209 |
| 5,496,787 | 3/1996 | Hatano et al. | 502/209 |
| 5,510,308 | 4/1996 | Kourtakis | 502/209 |
| 5,847,163 | 12/1998 | Mazzoni et al. | 549/243 |
| 5,885,919 | 3/1999 | Bortinger | 502/209 |
| 5,922,637 | 7/1999 | Bortinger | 502/209 |
| 5,945,368 | 8/1999 | Felthouse et al. | 502/209 |

OTHER PUBLICATIONS

Applied Catalysts 72 (1991) 1–32, Graham J. Hutchings, "Effect of promoters and reactant concentration on the selective oxidation of n–butane to maleic anhydride using vanadium phosphorus oxide catalysts" Sep. 1990.

Primary Examiner—Mark L. Bell
Assistant Examiner—Patricia L. Hailey
Attorney, Agent, or Firm—William C. Long

[57] ABSTRACT

A VPO catalyst precursor having the formula $(VO)HPO_4 aH_2 O M_m P_p O_y$ wherein M is at least one promoter element selected from the group consisting of elements from Groups IA, IB, IIA, IIIA, IIIB, IVA, IVB, VA, VB, VIA, VIB, and VIIIA of the Periodic Table of the Elements, and mixtures thereof, a is a number of at least about 0.3, m is a number of from about 0 to about 0.3, p is a number of from about 0 to about 0.3, any y corresponds to the amount of oxygen necessary to satisfy the valence requirements of all elements present, is activated by heating the catalyst precursor in an atmosphere selected from the group consisting of air, steam, inert gas, and mixtures thereof to a temperature not to exceed about 300° C., maintaining the catalyst precursor at this temperature and providing an atmosphere containing molecular oxygen, steam, and optionally an inert gas, increasing the temperature at a programmed rate of from about 0.5° C./min to about 15° C./min to a value effective to eliminate the water of hydration from the catalyst precursor, adjusting the temperature to a value greater than 350° C., but less than 550° C., and maintaining the adjusted temperature in a molecular oxygen/steam-containing atmosphere comprised of at least 1 vol % oxygen for a time effective to provide a vanadium oxidation state of from about +4.0 to about +4.5 and to complete transformation of the precursor to the active catalyst having the Formula $(VO)_2 P_2 O_7 M_{2m} P_{2p} O_y$ wherein M, m, p and y are defined above.

5 Claims, No Drawings

PHOSPHORUS/VANADIUM MALEIC ANHYDRIDE CATALYST PREPARATION

BACKGROUND OF THE INVENTION

1. Field of the Invention

The present invention relates to an improved method for the preparation of active vanadium/phosphorus mixed oxide catalysts which have special utility in the production of maleic anhydride.

2. Description of the Prior Art

Catalysts containing vanadium and phosphorus oxides have been used in the oxidation of 4-carbon atom hydrocarbons, such as n-butane, with molecular oxygen or oxygen containing gas to produce maleic anhydride. Conventional methods of preparing these catalysts involve reducing a pentavalent vanadium compound, and if desired, promoter element compounds under conditions which will provide or maintain vanadium in a valence state below +5 to form catalyst precursors which are recovered and converted to active catalyst.

U.S. Pat. No. 5,137,860 provides a comprehensive description of the prior art in this area. The patent shows the use of organic reducing agents as well as hydrogen chloride and teaches the use of activation procedures whereby the catalyst precursor is contacted at prescribed conditions with oxygen and steam mixtures and finally with a non-oxidizing steam atmosphere to produce an active catalyst.

U.S. Pat. No. 4,569,925 describes the preparation of vanadium/phosphorus mixed oxide catalysts by an organic solution method using anhydrous hydrogen chloride as an agent for the solubilization of the vanadium component, and teaches an activation procedure whereby the catalyst precursor is contacted not with air alone but with a mixture of air and a hydrocarbon such as methane, ethane, propane, butane and the like.

The synthesis of VPO catalysts can be carried out both in aqueous and in organic solvent media. Anhydrous conditions are preferred in the organic solvent method, and the synthesis in organic solvents is presently the preferred method due to the better performance of the catalyst. This is attributed to greater surface areas of the catalyst when prepared in organic solvent than in aqueous media (G. J. Hutchings, Applied Catalysis, 72(1991), 1-32 and references therein).

In the organic solvent method typically employing isobutanol, anhydrous HCl has been used as reducing agent for the $V_2O_5$. Other reducing agents have been used such as oxalic acid or organic alcohols such as allyl alcohol, benzyl alcohol and isobutanol which can be both the solvent and reducing agent. With HCl, the $V_2O_5$ is converted to an IBA (isobutyl alcohol) soluble material ($VOCl_2$) prior to the addition of phosphoric acid. In the absence of HCl, the $V_2O_5$ is not solubilized and the formation of the VPO catalyst is done heterogeneously on the suspended $V_2O_5$ in the organic solvent. The use of HCl has produced excellent catalysts but the residual chloride in the catalyst results in a chloride release during catalyst activation which is undesirable. This difficulty can be overcome by removing the chlorides through an additional step during the catalyst manufacturing.

An especially advantageous method for preparing a VPO catalyst for use in the production of maleic anhydride is described in copending application Ser. No. 09/108,223 filed Jul. 1, 1998, now U.S. Pat. No. 5,885,919, wherein the catalyst is prepared in an organic solvent procedure which involves the use of an additive such as dimethyl sulfoxide; especially good results are achieved where a bismuth catalyst promoter is also employed.

BRIEF DESCRIPTION OF THE INVENTION

In accordance with the present invention, a new and improved VPO mixed oxide catalyst activation procedure is provided whereby the VPO catalyst precursor, which can be formed by known procedures, is converted to the active catalyst form; the activation procedure comprises first heating the catalyst precursor in an atmosphere selected from the group consisting of air, steam, inert gas, and mixtures thereof to a temperature not to exceed about 300° C., maintaining the catalyst precursor at this temperature and providing an atmosphere containing molecular oxygen, steam, and optionally an inert gas, increasing the temperature at a programmed rate of from about 0.5° C./min to about 15° C./min to a value effective to eliminate the water of hydration from the catalyst precursor, adjusting the temperature to a value greater than 350° C., but less than 550° C., and maintaining the adjusted temperature in a molecular oxygen/steam-containing atmosphere comprised of at least 1 vol % oxygen for a time effective to provide a vanadium oxidation state of from about +4.0 to about +4.5 and for the transformation of the precursor to the active catalyst.

DETAILED DESCRIPTION OF THE INVENTION

The VPO catalyst precursors which are converted to the active catalyst form in accordance with the invention are prepared by known procedures such as are illustratively shown in said copending application Ser. No. 09/108,223 filed Jul. 1, 1998, or in U.S. Pat. No. 5,137,860, or by other non-corrosive preparations using the organic solvent method to prepare VPO catalyst precursors.

In accordance with the present invention, precursors are converted to the active catalyst form by first heating the precursor to a temperature not to exceed about 300° C. under an atmosphere of air, steam, inert gas, or mixtures. The precursors are maintained at this temperature and an atmosphere containing molecular oxygen, steam and optionally an inert gas is provided, the atmosphere being generally represented by the formula $(O_2)_x(H_2O)_y(IG)_z$ wherein IG is an inert gas and x, y, and z represent mol percent of the $O_2$, $H_2O$, and IG components, respectively, in the molecular oxygen/steam-containing atmosphere, with x having a value greater than zero (0) mol %, but less than 100 mol %, y having a value greater than zero (0) mol %, but less than 100 mol %, and z having a value representing the balance of the molecular oxygen/steam-containing atmosphere. The temperature is then increased at a programmed rate of from about 0.5° C./min to about 15° C./min to a value effective to eliminate the water of hydration from the catalyst precursor while minimizing the exotherm of the catalyst bed. Finally the temperature is adjusted to a value greater than 350° C., but less than 550° C., and the catalyst is maintained at the adjusted temperature in a molecular oxygen/steam-containing atmosphere containing more than 1 vol %, preferably more than 2 vol % and most desirably 3-8 vol % oxygen for a time effective to provide a vanadium oxidation state of from about +4.0 to about +4.5 and to complete transformation of the precursor to the activated catalyst. The atmosphere throughout the procedure can also comprise inert gas such as nitrogen, argon, helium, carbon dioxide and the like.

The activation procedure can be carried out at essentially atmospheric pressure or at elevated pressure.

Generally speaking, the activation procedure of the invention results in the transformation of a catalyst precursor represented by the formula $(VO)HPO_4 aH_2O M_m P_p O_y$, wherein M is at least one promoter element selected from the group consisting of elements from Groups IA, IB, IIA, IIB, IIIA, IIIB, IVA, IVB, VA, VB, VIA, VIB, and VIIIA of the Periodic Table of the Elements, and mixtures thereof, a is a number of at least about 0.3, m is a number of from about 0 to about 0.3, p is a number of from about 0 to about 0.3, any y corresponds to the amount of oxygen necessary to satisfy the valence requirements of all elements present, into an active catalyst represented by the formula $(VO)_2P_2O_7 M_{2m} P_{2p} O_y$ wherein M, m, p and y are as defined above.

Especially preferred is the method for the preparation of a phosphorus/vanadium/oxygen catalyst which is especially useful in the oxidation of n-butane to maleic anhydride wherein a vanadium compound in the +5 valence state, eg. vanadium pentoxide, is reduced in an organic medium which contains an organic sulfoxide additive which participates in vanadium reduction, and is reacted with concentrated phosphoric acid. The invention can be carried out in a single step, thus greatly simplifying catalyst preparation. After formation of the catalyst precursor, the precursor can be converted to the active form in accordance with the current invention.

Organic sulfoxide modifying agents which are employed in the invention have the formula:

wherein R and $R_1$ are the same or different groups having 1–8 carbon atoms selected from alkyl, substituted alkyl, aryl and substituted aryl groups. Preferred are sulfoxides wherein each of R and $R_1$ are alkyl groups having 1–4 carbon atoms and especially preferred are sulfoxides wherein each of R and $R_1$ is an alkyl group having 1–2 carbon atoms. dimethyl sulfoxide is preferred, other illustrative sulfoxides are methyl ethyl sulfoxide, diethyl sulfoxide, di-isopropyl sulfoxide, di-n-butyl sulfoxide, and the like.

The role of the organic sulfoxide in the preparation of catalyst and the nature of the mechanism by which catalyst performance is improved are not clearly understood. It is possible that the sulfoxide plays a role in the oxidation/reduction reactions during the catalyst formation. When the product is recovered there is a strong smell of a sulfur compound which is not observed without use of organic sulfoxide and is not present in the initial reaction mixture. Organic sulfoxide can both undergo oxidation to the sulfone, but also possibly can be reduced to the sulfide in our reaction mixture.

In carrying out this embodiment vanadium pentoxide in finely divided form is added to an organic solvent medium to which is also added an effective amount of the organic sulfoxide. Suitable solvents are alcohols known in this art such as, for example, a primary or secondary alcohol including methanol, ethanol, 1-propanol, 2-propanol, butanol, 2-butanol, 2, methyl-1-propanol, 3-methyl-2-butanol, 2,2-dimethyl-1-propanol, 1-hexanol, 4-methyl-1-pentanol, 1-heptanol, 4-methyl-1-hexanol, 4-methyl-1-heptanol, benzyl alcohol, 1,2-ethanediol, glycerol, trimethylopropane, 4-methyl, 2-pentanone, diethylene glycol and trimethylene glycol or mixtures thereof. The alcohols can also function as reducing agents for the vanadium +5 compound.

Generally, the organic sulfoxide is used in an amount which corresponds to a ratio of mols sulfoxide to atoms of vanadium of 0.001 to 1 and preferably 0.001 to 0.5 mols sulfoxide per atom of vanadium.

It is advantageous to incorporate catalyst promoters or modifiers in the catalyst and compounds of these components can be conveniently added to the organic solvent mixture initially or at a later stage after the catalyst precursor has been formed. Any of the known promoters can be used although it is especially advantageous to use a combination of Zn, Li and Mo promoters which are conveniently added as soluble compounds to the organic solvent. Especially outstanding results are achieved where a bismuth promoter is used. Other promoters include those described in U.S. Pat. Nos. 3,980,585, 4,056,487, 4,515,904, 4,147,661, 4,418,003, and the like the disclosures of which are incorporated herein by references.

In especially preferred practice, concentrated phosphoric acid is also added to the vanadium containing organic solvent solution which also contains the dialkyl sulfoxide and optionally the promoter compound or compounds, and the resulting mixture is digested at about 20 to 200° C. for a period of 1 to 24 hours.

In a less preferred embodiment, the phosphoric acid can be added after the vanadium pentoxide has been reduced in the organic solvent solution and the resulting mixture then digested to form the catalyst precursor.

The reduction and digestion procedures are carried out to form a VPO catalyst precursor which is represented by the formula $(VO)HPO_4 aH_2 O M_m P_p O_y$ wherein M is at least one promoter element selected from the group consisting of elements from Groups IA, IB, IIA, IIB, IIIA, IIIB, IVA, IVB, VA, VB, VIB, VIB, and VIIIA of the Periodic Table of the Elements, and mixtures thereof, a is a number of at least about 0.3, m is a number of from about 0 to about 0.3, p is a number of from about 0 to about 0.3, any y corresponds to the amount of oxygen necessary to satisfy the valence requirements of all elements present.

To obtain the mixed oxides of vanadium and phosphorus, phosphoric acid of approximately 100% $H_3PO_4$ (98 to 101%) is added. Superphosphoric acid (105–115%) can also be used while maintaining the desired P/V rate. Digestion of the vanadium compound is discerned by a change in the color of the reaction mixture to a blue color, the alcohol can be partially stripped or not and the precursor recovered by filtration and thereafter dried to produce the dried catalyst precursors.

The digestion of the vanadium compound in the phosphoric acid is normally conducted at reflux in order to form the VPO precursor during this step.

The final removal of alcohol and sulfoxide or derivative if used is carried out in a drying step in an oven at a temperature in the range of 100 to 180° C. for 1–24 hours. Lower temperatures and longer times can be used. Reduced pressure can also be applied during the drying step. Following drying, calcination of the dried catalyst precursor is carried out at a temperature in the range of about 200 to 300° for a sufficient period to improve the catalytic properties of the composition and remove volatile materials, usually 1–15 hours. The catalyst powder after the calcination step or even after the drying step is mixed with a lubricant such as graphite and fabricated to the desired geometric shape. Following calcination, the catalyst precursors are activated by the procedure of the invention as described above.

Preferred catalyst precursors may contain one of more promoters including Zn, Mo, Li, and Bi.

When Zn promoter is used, generally the atomic ratio of Zn to vanadium is in the range of 0.001 to 0.15:1, however it has been found that lower ratios of zinc/vanadium produce the most active catalyst and compositions containing Zn/V mole ratio in the range of 0.01 to 0.07 are preferred.

Where lithium is used, lithium component is present at an atomic ratio of 0.001 to 0.15/1, Li/V. Where molybdenum is used, the Mo/V atomic ratio is suitably 0.005 to 0.10, Mo/V.

Bismuth is a preferred promoter and is conveniently used in an atomic ratio of B/V in the range 0.001 to 0.15/1, preferably 0.005 to 0.07/1.

The modifier components are added as the compound thereof such as acetates, acetylacetonates, carbonates, chlorides, bromides, oxides, hydroxides, phosphates and the like, e.g. a bismuth salt of an organic acid or mixture of organic acids such as bismuth ethyl hexanoate, zinc acetyl acetonate, zinc acetate, lithium acetate, lithium carbonate, lithium oxide, or lithium orthophosphate and the like.

The molybdenum compound may be dissolved in an organic solvent, as described above or water and added to the reaction mixture. The solvent containing the molybdenum compound may be added with the other modifiers or at different times. The use of a soluble molybdenum compound dissolved in a solvent according to the present invention for addition to the reaction mixture has been found to be particularly effective in dispersing the molybdenum throughout the mixture and the final dried catalyst. Some examples of suitable soluble molybdenum catalyst include phosphomolybdic acid, ammonium molybdate (VI) tetrahydrate, lithium molybdate, molybdenum tetrabromide, molybdenum trioxyhexachloride and the like.

As an essential aspect of the present invention, the catalyst precursor formed as above indicated or by conventional procedures is activated by the activation procedure of the present invention.

The catalyst precursor is first heated at temperatures not exceeding 300° C. under an atmosphere which can be air, steam, inert gas, or a mixture for a time generally of 1–24 hours.

Following this, an atmosphere containing molecular oxygen, steam and optionally an inert gas is provided as above indicated and the temperature is increased at a rate of about 0.5° C. to 15° C. per minute to a value effective to eliminate water of hydration from the catalyst precursor, eg. 350° C. to 550° C., preferably 400° C. to 450° C.

The precursor is maintained at the adjusted temperature under an oxygen and steam containing atmosphere to complete vanadium conversion to an oxidation state of about +4.0 to about +4.5 and for the transformation of the precursor to the active catalyst which has the formula $(VO)_2P_2O_7M_{2m}P_{2p}O_y$ wherein M, m, p and y are as defined above. It is essential in this step that the atmosphere contain at least 1 vol % oxygen up to about 15 vol % oxygen, preferably at least 2 vol % oxygen and desirably 3–8 vol % oxygen. It is important to minimize the exotherm during this process.

The catalyst may be employed as pellets, disc, flakes, wafers, or any other convenient shape which will facilitate its use in the tubular reactors employed for this type of vapor phase reaction. For example the catalyst may be prepared as tablets having a hole or bore therethrough as disclosed in U.S. Pat. No. 4,283,307 which is incorporated herein. The material can be deposited on a carrier. Although fixed bed tubular reactors are standard for this type of reaction, fluidized beds are frequently used for oxidation reactions, in which case the catalyst particle size would be on the order of about 10 to 150 microns.

The use of this class of catalyst for the partial oxidation of $C_4$–$C_{10}$ hydrocarbons to the corresponding anhydrides is generally recognized. They have been widely considered for the conversion of normal $C_4$ hydrocarbons, both the alkane, n-butane, and alkene, and alkene, n-butane, for the production of maleic anhydride, which has a wide commercial usage.

The oxidation of the n-$C_4$ hydrocarbon to maleic anhydride may be accomplished by contacting e.g. n-butane in low concentrations in oxygen with the described catalyst. Air is entirely satisfactory as a source of oxygen, but synthetic mixtures of oxygen and diluent gases, such as nitrogen also may be employed. Air enriched with oxygen may be employed.

The gaseous feed stream to the standard tubular oxidation reactors normally will contain air and about 0.5 to about 3.0 mole percent hydrocarbons such as n-butane. About 1.0 to about 2.5 mole percent of the n-$C_4$ hydrocarbon are satisfactory for optimum yield of product for the process of this invention. Although higher concentrations may be employed, explosive hazards may be encountered except in fluidized bed reactors where concentrations of up to about 4 or 5 mole percent can be used without explosive hazard. Lower concentrations of $C_4$, less than about one percent, or course, will reduce the total productivity obtained at equivalent flow rates and thus are not normally economically employed.

The flow rate of the gaseous stream through the reactor may be varied within rather wide limits but a preferred range of operations is at the rate of about 10 to 300 grams of $C_4$ per liter of catalyst per hour and more preferably about 50 to about 250 grams of $C_4$ per liter of catalyst per hour. Residence times of the gas stream will normally be less than about 4 seconds, more preferably less than about one second, and down to a rate where less efficient operations are obtained. A preferred feed for the catalyst of the present invention for conversion to maleic anhydride is a n-$C_4$ hydrocarbon comprising a predominant amount of n-butane and more preferably at least 90 mole percent n-butane.

A variety of reactors will be found to be useful and multiple tube heat exchanger type reactors are quite satisfactory. The tubes of such reactors may vary in diameter from about ¼" to about 3", and the length may be varied from about 3 to about 18 or more feet. The oxidation reaction is an exothermic reaction and, therefore, relatively close control of the reaction temperature should be maintained. It is desirable to have the surface of the reactors at a relatively constant temperature and some medium to conduct heat from the reactors is necessary to aid temperature control. Such media may be Woods metal, molten sulfur, mercury, molten lead, and the like, but it has been found that eutectic salt baths are completely satisfactory. One such salt bath is a sodium nitrate-sodium nitrite-potassium nitrite eutectic constant temperature mixture. An additional method of temperature control is to use a metal block reactor whereby the metal surrounding the tube acts as a temperature regulating body. As will be recognized by one skilled in the art, the heat exchange medium may be kept at the proper temperature by heat exchangers and the like. The reactor or reaction tubes may be iron, stainless steel, carbon steel, nickel, glass tubes have excellent long life under the conditions for the reactions described herein. Normally, the reactors contain a preheat zone of an inert material such as ¼' Alundum pellets, inert ceramic balls, nickel balls or chips and the like, present at about ½ to ¹/₁₀ the volume of the active catalyst present.

The temperature of reaction may be varied within some limits, but normally the reaction should be conducted at temperatures within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than about 100° C. above the salt bath temperature. The temperature in the reactor, of course, will also depend to some extent upon the size of the reactor and the $C_4$ concentration. Under usual operating conditions in a preferred procedure, the temperature in the center of the reactor, measured by thermocouple, is about 365° C. to about 550° C. The range of temperature preferably employed in the reactor, measured as above, should be from about 380° C. to about 515° C. and the best results are ordinarily obtained at temperatures from about 380° C. to about 475° C. Described another way, in terms of salt bath reactors with carbon steel reactor tubes about 1.0" in diameter, the salt bath temperature will usually be controlled between about 350° C. to about 550° C. Under normal conditions, the temperature in the reactor ordinarily should not be allowed to go above about 475° C. for extended lengths of time because of decreased yields and possible deactivation of the catalyst.

The reaction may be conducted at atmospheric, super atmospheric or below atmospheric pressure. The exit pressure will be at least slightly higher than the ambient pressure to insure a positive flow from the reaction. The pressure of the gases must be sufficiently high to overcome the pressure drop through the reactor.

The maleic anhydride may be recovered in a number of ways well known to those skilled in the art. For example, the recovery may be by direct condensation or by absorption in suitable media, with subsequent separation and purification of the maleic anhydride.

EXAMPLE 1

Into a 12 liter round flask equipped with a mechanical stirrer, thermowell, Dean Stark trap with a condenser and a heating mantle were charged 6452 ml anhydrous isobutanol, 1613 ml benzyl alcohol, 70 grams of DMSO (Dimethyl sulfoxide), 815.1 grams $V_2O_5$, 66.9 grams of 28% Bi Hex-Cem (this is a Bi salt of 2 ethyl hexanoic acid in a mineral spirits carrier). About 1098 g of 100% phosphoric acid were added slowly into the reaction mixture while stirring.

The reaction mixture was brought to ref lux which was continued overnight. Thereafter, about 4032 ml distillate were removed and the reaction mixture was cooled down and filtered. The product cake was divided in two and each part was washed with about 700–1000 cc of fresh IBA (isobutyl alcohol). The product was then dried in the oven at 110° C. for 10 hours and finally at 150° C. for 16 hours. The dry cake was crushed and calcined at 220° C. for 3 hours and then at 260° C. for another 3 hours. The calcined powder was mixed with 4% graphite and was formed into $\frac{3}{16}$"×$\frac{3}{16}$" tablets with a $\frac{1}{16}$" I.D. hole struck therethrough. The catalyst was activated in Unit A.

Unit A consists of a single 9" OD meshed tray on which the catalyst pellets are supported. The tray was placed in a stainless steel metal unit which was then placed in an oven which had good temperature control. The gases entering the unit were preheated before passing through the catalyst bed. The tray in this unit was loaded with 425 g of shaped catalyst and was activated by the procedures described below.

A gas flow consisting by volume of 6.5% oxygen/nitrogen balance was passed through the catalyst bed while the oven was heated from room temperature to 275° C. in 75 minutes and held for 1 hour. During this period the catalyst bed reached the oven temperature. Thereafter, steam was introduced into the gas stream to obtain a gas atmosphere composition by volume of: 50% steam, 6.5% oxygen and the balance nitrogen. The oven temperature was raised to 425° C. in 38 minutes and held 10–30 minutes for the bed temperature to equilibrate with the oven temperature. The oven temperature was then held for another 7 hours under these conditions. At the end of this period the heating of the oven heating was discontinued and the catalyst bed was cooled down under the same gas mixture to 250° C. Thereafter, the steam was removed, and the catalyst bed was cooled to room temperature under dry gas containing 6.5% oxygen/nitrogen balance. The catalyst performance is shown in Table 1.

EXAMPLE 2

A fresh catalyst precursor prepared by the procedures described in Example 1 was activated in unit A by the following procedures.

A gas flow consisting by volume of 6.5% oxygen/nitrogen balance was passed through the catalyst bed while the oven was heated from room temperature to 275° C. in 75 minutes and held for 1 hour. During this period the catalyst bed reached the oven temperature. Thereafter, steam was introduced into the gas stream to obtain a gas composition by volume of: 50% steam, 6.5% oxygen and the balance nitrogen. The oven temperature was raised to 425° C. in 38 minutes and held 10–30 minutes for the bed temperature to equilibrate with the oven temperature and the oven temperature was held for another 3.5 hours under these conditions. The oxygen level was then reduced to 3% O2 by volume while maintaining 50% steam in the gas mixture, the balance being nitrogen and the oven temperature was held for another 3.5 hours under these conditions. Thereafter, the steam was removed, and the catalyst bed cooled to room temperature under dry gas containing 3% oxygen/nitrogen balance by volume. The catalyst performance is shown in Table 1.

EXAMPLE 3

A fresh catalyst prepared by the procedures described in Example 1 was activated in unit A by the following procedures.

A gas flow consisting by volume of 21% oxygen/nitrogen balance was passed through the catalyst bed while the oven was heated from room temperature to 275° C. in 75 minutes and held for 1 hour at that temperature. During this period the catalyst bed reached the oven temperature. Thereafter, steam was introduced into the gas stream to obtain a gas composition by volume of: 50% steam, 10.5% O2 and the balance nitrogen. The oven temperature was raised to 425° C. in 38 minutes and held 10–30 minutes for the bed temperature to equilibrate with the oven temperature. The oven temperature was held for another 1 hour under these conditions and then the oxygen level was reduced to 6.5% oxygen while maintaining 50% steam in the gas mixture and the balance nitrogen, the percentages being volume percent. The oven was held at 425° C. under this gas composition for 6 hours. At the end of this period the oven heating was stopped and the catalyst bed cooled under the same gas mixture to 250° C. Thereafter, the steam was removed, and the catalyst bed cooled to room temperature under dry gas containing by volume 6.5% oxygen/nitrogen balance. The catalyst performance is shown in Table 1.

EXAMPLE 4

Into a 12 liter round flask equipped with a mechanical stirrer, thermowell, Dean Stark trap with a condenser and a heating mantle were charged 6452 ml anhydrous isobutanol, 1613 ml benzyl alcohol, 70 grams of DMSO (Dimethyl sulfoxide), 815.1 grams $V_2O_5$ 66.9 grams of 28% Bi Hex-Cem (this is a Bi salt of 2 ethyl hexanoic acid in a mineral spirits carrier). About 1098 g of 100% phosphoric acid were added slowly into the reaction mixture while stirring.

The reaction mixture was brought to ref lux which was continued overnight. Thereafter, the reaction mixture was cooled down, 80 ml of 30% hydrogen peroxide were added while stirring. After about 30 minutes of stirring the reaction mixture was filtered. The solids product was then dried in the oven at 110° C. for 10 hours and finally at 150° C. for 16 hours. The dry cake was crushed and calcined at 220° C. for 3 hours and then at 260° C. for another 3 hours. The calcined powder was mixed with 4% graphite and was formed into 3/16"×3/16" tablets with a 1/16" I.D. hole struck there through. The catalyst was activated in Unit A by the same procedures described in Example 3. The catalyst performance is shown in Table 1.

TABLE 1

| Example | 1 | 2 | 3 | 4 |
|---|---|---|---|---|
| Hours | 441 | 453 | 488 | 482 |
| Salt ° C. | 378 | 37S | 381 | 384 |
| Hot Spot ° C. | 428 | 443 | 434 | 440 |
| % Butane | 1.29 | 1.30 | 1.31 | 1.30 |
| % Conversion | 79.7 | 79.9 | 79.1 | 79.7 |
| % Selectivity | 69.3 | 69.4 | 70.6 | 69.9 |
| Wt % Yield | 93.4 | 93.4 | 94.3 | 94.2 |

It can be seen from the above results that the catalyst prepared in accordance with the present invention demonstrates excellent performance for the conversion of butane to maleic anhydride.

What is claimed is:

1. The process for activating VPO maleic anhydride catalyst precursor having the formula $(VO)HPO_4aH_2OM_mP_pO_y$ wherein M is at least one promoter element selected from the group consisting of elements from Groups IA, IB, IIA, IIB, IIIA, IIIB, IVA, IVB, VA, VB, VIA, VIB, and VIIIA of the Periodic Table of the Elements, and mixtures thereof, a is a number of at least about 0.3, m is a number of from about 0 to about 0.3, p is a number of from about 0 to about 0.3, any y corresponds to the amount of oxygen necessary to satisfy the valence requirements of all elements present which comprises heating the catalyst precursor in an atmosphere selected from the group consisting of air, steam, inert gas, and mixtures thereof to a temperature not to exceed about 300° C., maintaining the catalyst precursor at this temperature and providing an atmosphere containing molecular oxygen, steam, and optionally an inert gas, increasing the temperature at a rate of from about 0.5° C./min to about 15° C./min to a value effective to eliminate the water of hydration from the catalyst precursor, adjusting the temperature to a value greater that 350° C., but less than 550° C., and maintaining the adjusted temperature in a molecular oxygen/steam-containing atmosphere comprised of at least 1 vol % oxygen for a time effective to provide a vanadium oxidation state of from about +4.0 to about +4.5 and to complete transformation to the active catalyst having the formula $(VO)_2P_2O_7M_{2m}P_{2p}O_y$ wherein M, m, p and y as defined above.

2. The process of claim 1 wherein the said molecular oxygen/steam-containing atmosphere is comprised of at least 2 vol % oxygen.

3. The process of claim 1 wherein the said molecular oxygen/steam-containing atmosphere is comprised of 3–8 vol % oxygen.

4. The process for activating VPO maleic anhydride catalyst precursor formed by reduction of pentavalent vanadium in the presence of a dialkyl sulfoxide, said precursor having the formula $(VO)HPO_4aH_2OM_mP_pO_y$ wherein M is at least one promoter element selected from the group consisting of elements from Groups IA, IB, IIA, IIB, IIIA, IIIB, IVA, IVB, VA, VB, VIA, VIB, and VIIIA of the Periodic Table of the Elements, and mixtures thereof, a is a number of at least about 0.3, m is a number of from about 0 to about 0.3, p is a number of from about 0 to about 0.3, any y corresponds to the amount of oxygen necessary to satisfy the valence requirements of all elements present which comprises heating the catalyst precursor in an atmosphere selected from the group consisting of air, steam, inert gas, and mixtures thereof to a temperature not to exceed about 300° C., maintaining the catalyst precursor at this temperature and providing an atmosphere containing molecular oxygen, steam, and optionally an inert gas, increasing the temperature at a rate of from about 0.5° C./min to about 15° C./min to a value effective to eliminate the water of hydration from the catalyst precursor, adjusting the temperature to a value greater that 350° C., but less than 550° C., and maintaining the adjusted temperature in a molecular oxygen/steam-containing atmosphere comprised of at least 1 vol % oxygen for a time effective to provide a vanadium oxidation state of from about +4.0 to about +4.5 and to complete transformation to the active catalyst having the formula $(VO)_2P_2O_7M_{2m}P_{2p}O_y$ wherein M, m, p and y as defined above.

5. The process of claim 4 wherein the catalyst precursor is formed by reduction of pentavalent vanadium in the presence of dimethyl sulfoxide.

* * * * *